US012667828B2

(12) United States Patent
Mizubayashi et al.

(10) Patent No.: US 12,667,828 B2
(45) Date of Patent: Jun. 30, 2026

(54) HYDROCARBON SYNTHESIS CATALYST, METHOD FOR MANUFACTURING SAME, AND METHOD FOR SYNTHESIZING HYDROCARBONS

(71) Applicants: YKK Corporation, Tokyo (JP); NATIONAL UNIVERSITY CORPORATION UNIVERSITY OF TOYAMA, Toyama (JP)

(72) Inventors: Mai Mizubayashi, Kurobe (JP); Naoki Tomono, Kurobe (JP); Yuka Katayama, Kurobe (JP); Jingdi Cao, Kurobe (JP); Noritatsu Tsubaki, Toyama (JP); Guohui Yang, Toyama (JP)

(73) Assignees: YKK Corporation, Tokyo (JP); National University Corporation University of Toyama, Toyama (JP)

( * ) Notice: Subject to any disclaimer, the term of this patent is extended or adjusted under 35 U.S.C. 154(b) by 495 days.

(21) Appl. No.: 18/202,648

(22) Filed: May 26, 2023

(65) Prior Publication Data

US 2023/0381754 A1 Nov. 30, 2023

(30) Foreign Application Priority Data

May 31, 2022 (JP) ................................. 2022-089175

(51) Int. Cl.
*B01J 23/86* (2006.01)
*B01J 35/30* (2024.01)
(Continued)

(52) U.S. Cl.
CPC ........... *B01J 23/866* (2013.01); *B01J 35/394* (2024.01); *B01J 35/40* (2024.01); *B01J 35/55* (2024.01);
(Continued)

(58) Field of Classification Search
CPC ...... B01J 23/866; B01J 35/394; B01J 35/613; B01J 2235/15; B01J 2235/30;
(Continued)

(56) References Cited

U.S. PATENT DOCUMENTS 7,598,295 B2 10/2009 Bromfield et al.
2015/0011801 A1 1/2015 Carter

FOREIGN PATENT DOCUMENTS

CN 1695803 A 11/2005
CN 107511152 A 12/2017
(Continued)

OTHER PUBLICATIONS

Combined Search and Examination Report, British Patent Application No. 2307839.7, Dec. 14, 2023, 7 pages.
(Continued)

*Primary Examiner* — Jafar F Parsa
(74) *Attorney, Agent, or Firm* — Kilpatrick Townsend & Stockton LLP

(57) ABSTRACT

A hydrocarbon synthesis catalyst is for reacting a raw material gas including hydrogen and carbon dioxide to convert to hydrocarbons, wherein when elemental analysis of a surface of the hydrocarbon synthesis catalyst to be brought into contact with the raw material gas is performed by energy dispersive X-ray spectroscopy (SEM-EDX), 15 to 65% by mass of Fe, 10 to 40% by mass of O, 0.04 to 30% by mass of Na, 0 to 15% by mass of Ni, and 5 to 30% by mass of Cr are detected.

19 Claims, 4 Drawing Sheets

(51) Int. Cl.

| | |
|---|---|
| *B01J 35/40* | (2024.01) |
| *B01J 35/55* | (2024.01) |
| *B01J 35/61* | (2024.01) |
| *B01J 37/00* | (2006.01) |
| *B01J 37/02* | (2006.01) |
| *B01J 37/06* | (2006.01) |
| *B01J 37/14* | (2006.01) |
| *C07C 1/12* | (2006.01) |

(52) U.S. Cl.

CPC ......... *B01J 35/613* (2024.01); *B01J 37/0009* (2013.01); *B01J 37/0207* (2013.01); *B01J 37/0209* (2013.01); *B01J 37/06* (2013.01); *B01J 37/14* (2013.01); *C07C 1/12* (2013.01); *B01J 2235/00* (2024.01); *B01J 2235/15* (2024.01); *B01J 2235/30* (2024.01); *C07C 2523/86* (2013.01)

(58) Field of Classification Search

CPC .... B01J 2523/86; B01J 23/0862; B01J 23/86; C07C 1/12; C10G 2/32

See application file for complete search history.

(56) References Cited

FOREIGN PATENT DOCUMENTS

| | | | |
|---|---|---|---|
| CN | 107812521 | A | 3/2018 |
| CN | 110813305 | A | 2/2020 |
| JP | 2007-196187 | A | 8/2007 |
| JP | 2009-106863 | A | 5/2009 |
| JP | 2009-214077 | A | 9/2009 |
| JP | 2021-186724 | A | 12/2021 |

OTHER PUBLICATIONS

Office Action, Japanese Patent Application No. 2022-089175, Mar. 12, 2026, 8 pages.

HYDROCARBON SYNTHESIS CATALYST, METHOD FOR MANUFACTURING SAME, AND METHOD FOR SYNTHESIZING HYDROCARBONS

CROSS REFERENCE TO RELATED APPLICATIONS

The present invention claims the benefit of priority to Japanese Patent Application No. 2022-89175 filed on May 31, 2022 with the Japanese Patent Office, the entire contents of which are incorporated herein by reference in its entirety.

FIELD OF THE INVENTION

The present invention relates to a hydrocarbon synthesis catalyst and a method for manufacturing the same. The present invention also relates to a method for synthesizing hydrocarbons using a hydrocarbon synthesis catalyst.

BACKGROUND OF THE INVENTION

In recent years, with the aim of constructing a world of decarbonization and carbon resource recycling, various industries have actively engaged in the recycling of carbon dioxide, the chemical recycling of waste plastics, the effective use of natural gas, and the development of alternative energy sources to petroleum. In the maritime industry, the current situation is that cheap heavy fuel oil C is used as fuel for ships, which emits a large amount of carbon dioxide ($CO_2$). For this reason, under the greenhouse gas (GHG) reduction targets set by the International Maritime Organization (IMO), there is a demand for conversion to environmentally friendly ships represented by zero-emission ships, and methods of using fuels with low or zero $CO_2$ emissions such as LNG, methane, ammonia, and hydrogen, methods of using wind power or batteries, and methods of recovering $CO_2$ onboard are being studied. Among the above methods, LNG fuel has been put into practical use, but the other methods still have problems such as technological development and fuel sharing infrastructure construction, and there is a large room for technological development.

On the other hand, a technique is known in which carbon sources such as carbon monoxide or carbon dioxide, and hydrogen are used as raw materials to synthesize a hydrocarbon or an alcohol with a catalyst.

In Japanese Patent Application Publication No. 2009-214077 (Patent Literature 1), there is disclosed a Cu-containing catalyst for methanol synthesis, which is used in synthesizing methanol via formic acid ester from a raw material gas in the presence of an alcohol solvent, the raw material gas comprising carbon monoxide, or carbon monoxide and carbon dioxide; and hydrogen. In Patent Literature 1, Cu/ZnO, Cu/MgO, Cu/CeO, Cu/MnO and Cu/ReO are described as catalyst components to be combined with Cu.

In Japanese Patent Application Publication No. 2009-106863 (Patent Literature 2), there is disclosed an FT synthesis method for synthesizing isoparaffin by contacting a gas containing carbon monoxide and hydrogen with a catalyst, the method comprising using a catalyst for FT synthesis in which a plurality of nanoparticles is dispersedly carried or coated on a surface of a powdery carrier. As the powdery carrier, at least one material selected from the group consisting of zeolites, silica gel, alumina and titanium oxide is disclosed. As the nanoparticles, metal particles of at least one of Co and Ru, or particles comprising said metal particles are disclosed.

In Japanese Patent Application Publication No. 2007-196187 (Patent Literature 3), there is disclosed a catalyst obtained by coating a surface of a particulate solid with a membrane composed of beta zeolite. The catalyst can produce a liquid fuel with lower methane selectivity and $CO_2$ selectivity, and higher isoparaffin yield in a single step from a synthesis gas.

In Japanese Patent Application Publication No. 2021-186724 (Patent Literature 4), there is disclosed a shaped article of catalyst manufactured by a three-dimensional modeling method, which contains a catalyst raw material as a main component and has flow paths for synthetic raw materials. In the Examples of Patent Literature 4, it is described that hydrocarbons were synthesized from $CO_2$ and $H_2$ using a shaped article of Fe catalyst having a composition of Fe-65.6% by mass, Ni-17.8% by mass, Co-10.1% by mass, Mo-5.4% by mass, and Ti-1.1% by mass.

PRIOR ART

Patent Literature

[Patent Literature 1] Japanese Patent Application Publication No. 2009-214077
[Patent Literature 2] Japanese Patent Application Publication No. 2009-106863
[Patent Literature 3] Japanese Patent Application Publication No. 2007-196187
[Patent Literature 4] Japanese Patent Application Publication No. 2021-186724

SUMMARY OF THE INVENTION

In order to put environmentally friendly ships into practical use, it is desirable to develop a technology for producing hydrocarbons that can be used as fuel from $CO_2$ recovered on board. For this purpose, a technique is required that uses $CO_2$ as a raw material to synthesize hydrocarbons having 5 or more carbon atoms that are easy to handle as fuel. However, the catalysts described in the above Patent Literatures have a problem of being expensive because they contain a large amount of rare metals, or a problem of having low selectivity to liquid hydrocarbons. Therefore, there is still room for improvement.

In view of the above circumstances, in one embodiment of the present invention, it is an object to provide a hydrocarbon synthesis catalyst that can synthesize hydrocarbons having 5 or more carbon atoms with high selectivity using $CO_2$ and $H_2$ as raw materials and that can be manufactured from inexpensive materials. In another embodiment of the present invention, it is an object to provide a method for manufacturing such a hydrocarbon synthesis catalyst. Further, in yet another embodiment of the present invention, it is an object to provide a method for synthesizing hydrocarbons using such a hydrocarbon synthesis catalyst.

In order to solve the above problems, as a result of intensive studies by the present inventors, it has been found that selectivity to hydrocarbons with a carbon number of 5 or more when synthesizing hydrocarbons using $CO_2$ and $H_2$ as raw materials can be significantly improved by using an oxidized Fe—Cr alloy moderately impregnated with Na as a catalyst. The present invention has been completed based on the above finding, and is exemplified as follows.

[1] A hydrocarbon synthesis catalyst for reacting a raw material gas comprising hydrogen and carbon dioxide to convert to hydrocarbons, wherein when elemental analysis of a surface of the hydrocarbon synthesis catalyst to be brought into contact with the raw material gas is performed by energy dispersive X-ray spectroscopy (SEM-EDX), 15 to 65% by mass of Fe, 10 to 40% by mass of 0, 0.04 to 30% by mass of Na, 0 to 15% by mass of Ni, and 5 to 30% by mass of Cr are detected.

[2] The hydrocarbon synthesis catalyst according to [1], wherein when the surface of the hydrocarbon synthesis catalyst to be brought into contact with the raw material gas is analyzed by an X-ray diffraction method, oxides with Fe valences of +2 and/or +3 are detected.

[3] The hydrocarbon synthesis catalyst according to [1] or [2], wherein when the surface of the hydrocarbon synthesis catalyst to be brought into contact with the raw material gas is analyzed by an X-ray diffraction method, a ratio $(I_2/I_1)$ is in a range of 0.02 to 3.0, in which $I_1$ is a peak area in a range of $2\theta=44°$ to $45°$ representative of Fe—Cr alloy, and $I_2$ is a peak area in a range of $2\theta=35°$ to $36°$ representative of $Fe_2O_3$.

[4] The hydrocarbon synthesis catalyst according to any one of [1] to [3], wherein when the surface of the hydrocarbon synthesis catalyst to be brought into contact with the raw material gas is analyzed by an X-ray diffraction method, a ratio $(I_3/I_1)$ is in a range of to 0.5, in which $I_1$ is a peak area in a range of $2\theta=44°$ to $45°$ representative of Fe—Cr alloy, and $I_3$ is a peak area in a range of $2\theta=30°$ to $31°$ representative of $FeCr_2O_4$.

[5] The hydrocarbon synthesis catalyst according to any one of [1] to [4], wherein when elemental analysis of the surface of the hydrocarbon synthesis catalyst to be brought into contact with the raw material gas is performed by energy dispersive X-ray spectroscopy (SEM-EDX), 0.05 to 4% by mass of Na is detected.

[6] The hydrocarbon synthesis catalyst according to any one of [1] to [5], wherein when elemental analysis of the surface of the hydrocarbon synthesis catalyst to be brought into contact with the raw material gas is performed by energy dispersive X-ray spectroscopy (SEM-EDX), 2 to 9% by mass of Ni is detected.

[7] The hydrocarbon synthesis catalyst according to any one of [1] to [6], wherein the hydrocarbon synthesis catalyst is in a powder form.

[8] The hydrocarbon synthesis catalyst according to [7], wherein a BET specific surface area of the hydrocarbon synthesis catalyst is 10 to 20 $m^2/g$.

[9] The hydrocarbon synthesis catalyst according to any one of [1] to [8], wherein the hydrocarbon synthesis catalyst is provided in a form of a shaped article comprising one or more flow paths penetrating from one end surface to the other end surface, wherein a surface of the one or more flow paths constitutes the surface of the hydrocarbon synthesis catalyst to be brought into contact with the raw material gas.

[10] The hydrocarbon synthesis catalyst according to [9], wherein a BET specific surface area of the surface of the one or more flow paths is 5 to 15 $m^2/g$.

[11] A method for manufacturing the hydrocarbon synthesis catalyst according to [7] or [8], the method comprising:

a step A1 of preparing a Fe—Cr alloy powder comprising 50 to 90% by mass of Fe, 10 to 20% by mass of Cr, and 0 to 20% by mass of Ni;

a step A2 of impregnating the powder with Na to obtain a Na-impregnated powder; and a step A3 of firing the Na-impregnated powder in an oxygen-containing atmosphere at 380 to 880° C.

[12] The method for manufacturing the hydrocarbon synthesis catalyst according to [11], wherein the Fe—Cr alloy comprises 3 to 5% by mass of Ni.

[13] The method for manufacturing the hydrocarbon synthesis catalyst according to [11], wherein the Fe—Cr alloy is SUS630.

[14] The method for manufacturing the hydrocarbon synthesis catalyst according to any one of [11] to [13], further comprising a step A4 of pickling the powder between the step A1 and the step A2.

[15] A method for manufacturing the hydrocarbon synthesis catalyst according to [9] or [10], the method comprising:

a step B1 of preparing a Fe—Cr alloy powder comprising 50 to 90% by mass of Fe, 10 to 20% by mass of Cr, and 0 to 20% by mass of Ni;

a step B2 of shaping the powder using an additive manufacturing method into a shaped article comprising one or more flow paths penetrating from one end surface to the other end surface;

a step B3 of impregnating a surface of the one or more flow paths of the shaped article with Na to obtain a Na-impregnated shaped article; and a step B4 of firing the Na-impregnated shaped article in an oxygen-containing atmosphere at 380 to 880° C.

[16] The method for manufacturing the hydrocarbon synthesis catalyst according to [15], wherein the Fe—Cr alloy comprises 3 to 5% by mass of Ni.

[17] The method for manufacturing the hydrocarbon synthesis catalyst according to [15], wherein the Fe—Cr alloy is SUS630.

[18] The method for manufacturing the hydrocarbon synthesis catalyst according to any one of [15] to [17], further comprising a step B5 of pickling the surface of the one or more flow paths of the shaped article between the step B2 and the step B3.

[19] A method for synthesizing hydrocarbons, comprising contacting a raw material gas comprising hydrogen and carbon dioxide with the surface of the hydrocarbon synthesis catalyst according to any one of [1] to [10] be brought into contact with the raw material gas, thereby reacting the raw material gas.

According to one embodiment of the present invention, there is provided a hydrocarbon synthesis catalyst that can synthesize hydrocarbons having 5 or more carbon atoms with high selectivity using $CO_2$ and $H_2$ as raw materials. In addition, since this hydrocarbon synthesis catalyst does not require many rare metals, it can be manufactured from inexpensive materials. Therefore, the catalyst is expected to play an important role in constructing a world of decarbonization and carbon resource recycling. In addition, by manufacturing three-dimensional shaped articles using the hydrocarbon synthesis catalyst as a raw material with additive manufacturing technology, it is possible to mass-produce catalyst shaped articles with high accuracy which once required high manufacturing technology and suffered large human errors. Furthermore, it is also possible to use the catalyst shaped article itself as a reactor, which contributes to downsizing of the reactor. By downsizing the reactor, it becomes easier to install the reactor on board, so it is considered that it will also contribute to the realization of a zero-emission ship that converts $CO_2$ recovered on board into fuel.

Figure 1A:
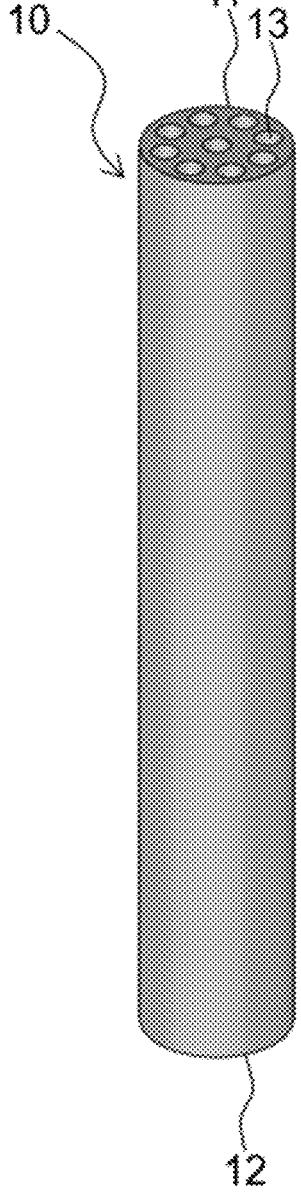
FIG. 1A is a schematic perspective view of one example of the hydrocarbon synthesis catalyst of the present invention.

DETAILED DESCRIPTION OF THE INVENTION (1. Hydrocarbon Synthesis Catalyst)

In one embodiment of the present invention, when elemental analysis of a surface of the hydrocarbon synthesis catalyst to be brought into contact with a raw material gas is performed by energy dispersive X-ray spectroscopy (SEM-EDX), 15 to 65% by mass of Fe, 10 to 40% by mass of O, 0.04 to 30% by mass of Na, 0 to 15% by mass of Ni, and 5 to 30% by mass of Cr are detected.

In the elemental analysis, Fe is preferably detected in an amount of 15 to 65% by mass, more preferably detected in an amount of 25 to 65% by mass, even more preferably detected in an amount of 35 to 65% by mass, and even more preferably detected in an amount of 45 to 65% by mass.

In the elemental analysis, O is preferably detected in an amount of 10 to 40% by mass, more preferably detected in an amount of 10 to 30% by mass, and even more preferably detected in an amount of 10 to 20% by mass.

In the elemental analysis, Na is preferably detected in an amount of 0.04 to 30% by mass, more preferably detected in an amount of 0.05 to 15% by mass, even more preferably detected in an amount of 0.05 to 10% by mass, even more preferably detected in an amount of 0.05 to 8% by mass, even more preferably detected in an amount of 0.05 to 6% by mass, and even more preferably detected in an amount of 0.05 to 4% by mass.

In the elemental analysis, Ni is preferably detected in an amount of 0 to 15% by mass, more preferably detected in an amount of 0 to 10% by mass, even more preferably detected in an amount of 1 to 9% by mass, and even more preferably detected in an amount of detected in an amount of 2 to 9% by mass.

In the above elemental analysis, Cr is preferably detected in an amount of 5 to 30% by mass, more preferably detected in an amount of 5 to 25% by mass, even more preferably detected in an amount of 5 to 20% by mass, and even more preferably detected in an amount of 10 to 20% by mass.

In the elemental analysis, the total concentration of Fe, O, Na, Ni, and Cr is preferably 85% by mass or more, and more preferably 90% by mass or more. There is no particular upper limit to the total concentration of Fe, O, Na, Ni, and Cr, and it may be 100% by mass. However, since impurity elements and additive elements may be included, the total concentration is usually 95% by mass or less, and typically 93% by mass or less.

In addition, in one embodiment of the present invention, when elemental analysis of a surface of the hydrocarbon synthesis catalyst to be brought into contact with a raw material gas is performed by energy dispersive X-ray spectroscopy (SEM-EDX), Si may be detected in an amount of 0 to 5.0% by mass, for example, 0.2 to 4.5% by mass; Al may be detected in an amount of 0 to 2.0% by mass, for example, 0.2 to 1.8% by mass; Mn may be detected in an amount of 0 to 2.5% by mass, for example, 0.2 to 2.0% by mass; Cu may be detected in an amount of 0 to 5% by mass, for example, 0 to 3.0% by mass; Nb may be detected in an amount of 0 to 1.0% by mass, for example, 0 to 0.9% by mass; Mo may be detected in an amount of 0 to 3.0% by mass, for example, 0.1 to 2.0% by mass.

The above elemental analysis by SEM-EDX was performed under the following conditions in the Examples.

Device: JSM-IT500HR/LA scanning electron microscope manufactured by JEOL Ltd.

Observation model: secondary electron image

Measurement voltage: 15 kV

Measurement current: 65 mA

Degree of vacuum: 9.99E-07 Pa

Sample preparation:

(1) For powders (including pellets), they are fixed to a holder with carbon tape.

(2) For shaped articles, it is cut with a fine cutter such that the length of the flow paths is 3 mm. Next, it is further divided into two pieces with a fine cutter along a cutting line that crosses the cross-section perpendicular to the length direction of the flow paths of the shaped article in order to expose at least one or more flow paths, thereby obtaining a test piece (if the shaped article is cylindrical, a semi-cylindrical test piece is obtained). Then, as organic oil is used when cutting, considering the possibility that a correct elemental analysis may not be possible due to the organic component adhering to the surface as contamination, the test piece is dried in vacuum at 250° C. for 2 to 4 hours before SEM-EDX measurement. Finally, the test piece from which the organic components have been removed is fixed to a holder.

EDX range setting: for powders, the surface of the powder, and for shaped articles, the surface of the flow path is magnified up to 70 or 120 times, and three or more areas each having an area of $0.100 \, mm^2$ are randomly enclosed in the field of view, and elemental quantitative analysis is performed for each area. The elements to be measured are limited to eleven kinds of Fe, O, Na, Ni, Cr, Si, Al, Mn, Cu, Nb and Mo. C is zero-corrected. Elemental mass percentages are determined as the average of three points.

In one embodiment of the present invention, when the surface of the hydrocarbon synthesis catalyst to be brought into contact with a raw material gas is analyzed by an X-ray diffraction method (XRD), oxides with Fe valences of +2 and/or +3 are detected. In more detail, it is preferable that a ratio $(I_2/I_1)$ is in the range of 0.02 to 3.0, in which $I_1$ is the peak area in the range of $2\theta=44°$ to $45°$ representative of Fe—Cr alloy, and $I_2$ is the peak area in the range of $2\theta=35°$ to $36°$ representative of $Fe_2O_3$. $I_2/I_1$ is more preferably in the range of 0.04 to 2.5, and even more preferably in the range of 0.05 to 2.5. In addition, it is preferable that a ratio $(I_3/I_1)$ is in the range of 0.02 to 0.5, in which $I_1$ is the peak area in the range of $2\theta=44°$ to $45°$ representative of Fe—Cr alloy, and $I_3$ is the peak area in the range of $2\theta=30°$ to $31°$ representative of $FeCr_2O_4$. $I_3/I_1$ is more preferably in the range of 0.02 to 0.2, and even more preferably in the range of 0.05 to 0.2.

The analysis by the above X-ray diffraction method was performed under the following conditions in the Examples.

Device: 3 kW X-ray generator Ultima IV manufactured by Rigaku Corporation

X-ray source: CuKα characteristic X (40 kV, 20 mA)

Scanning range: 5 to 90°

Scanning step: 0.02°

Integration time: 0.6 s/step

Sample preparation: prepared in the same manner as the sample preparation for elemental analysis by SEM-EDX as described above.

While not intending to limit the invention by any theory, considering the purpose of the present invention, FeOx/FeCx/Fe are required as catalytically active sites. It is presumed that iron oxides such as $Fe_2O_3$ and $FeCr_2O_4$ present on the surface of the catalyst have the effect of promoting the reaction in which $CO_2$ is converted to CO. In addition, Na present on the surface of the catalyst acts as a co-catalyst, which facilitates the conversion of iron oxides to iron carbides, and iron carbide is presumed to have the effect of promoting the reaction of CO and H to produce hydrocarbons having 5 or more carbon atoms. Furthermore, it is presumed that the presence of an appropriate amount of Na on the surface of the catalyst facilitates the adsorption of $CO_2$ and $H_2$ molecules on the surface of the catalyst, thereby promoting the reaction. In addition, the iron carbide is considered to be oxidized by excess $CO_2$ and the by-product $H_2O$ to return to iron oxide.

In one embodiment of the present invention, the hydrocarbon synthesis catalyst can be provided in the form of powder (the form of powder includes form of pellets). In that case, when the particle size distribution of the hydrocarbon synthesis catalyst is analyzed by a laser diffraction/scattering method, the volume-based median diameter (D50) is preferably 200 to 900 μm, more preferably 300 to 900 μm, and even more preferably 355 to 850 μm.

In one embodiment of the present invention, when the hydrocarbon synthesis catalyst is provided in the form of powder, it preferably has a BET specific surface area of 10 to 20 $m^2$/g, more preferably 15 to 17 $m^2$/g, in order to promote the reaction. The BET specific surface area of the hydrocarbon synthesis catalyst in the form of powder was measured under the following conditions in the Examples.

Device: Multi-specimen high-performance specific surface area/pore size distribution measuring device (3Flex-2MP manufactured by Micromeritics Instrument Corporation, USA)

Measurement method: gas adsorption method by constant volume method

Gas used: nitrogen

Figure 1B:
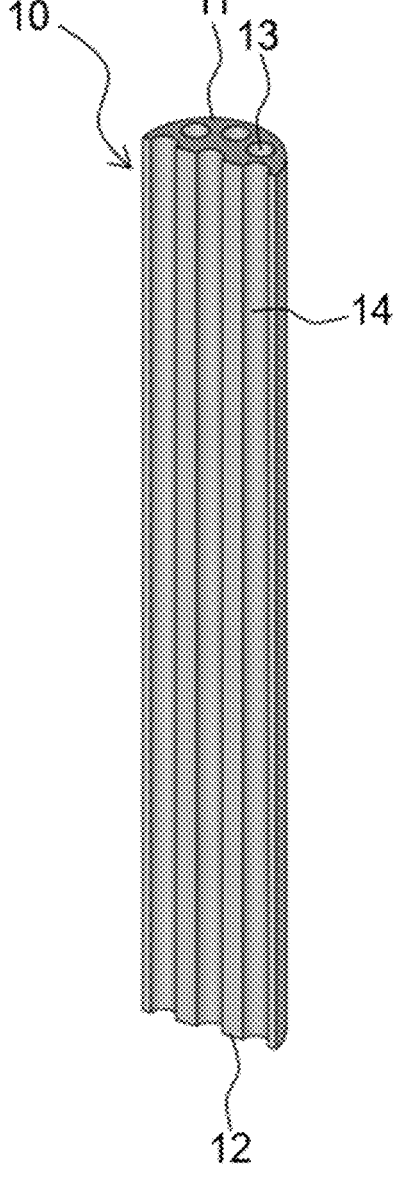
FIG. 1B is a schematic cross-sectional perspective view of the hydrocarbon synthesis catalyst shown in FIG. 1A cut along a plane passing through the central axis and parallel to the direction in which the flow paths extend.

Pretreatment: degassing the sample at 250° C. for 10 hours under vacuum conditions Sample measurement amount: about 0.1 g In one embodiment of the present invention, the hydrocarbon synthesis catalyst can be provided in the form of a shaped article. FIG. 1A shows a schematic diagram of one example of the hydrocarbon synthesis catalyst of the present invention when observed from one end surface. FIG. 1B is a schematic cross-sectional perspective view of the hydrocarbon synthesis catalyst shown in FIG. 1A cut along a plane passing through the central axis extending in the longitudinal direction and parallel to the flow paths. The illustrated hydrocarbon synthesis catalyst 10 comprises one or more flow paths 13 penetrating from one end surface 11 to the other end surface 12, and the surface 14 of flow paths 13 constitutes the surface of the hydrocarbon synthesis catalyst to be brought into contact with a raw material gas. The number of flow paths 13 is not particularly limited, and may be appropriately set according to the amount of raw material gas to be processed. For example, the number can be 1 to 11 (in FIG. 1A, the number is 9). The outer shape of the hydrocarbon synthesis catalyst 10 can be, for example, a cylinder such as a cylinder, a polygonal prism (quadrangular prism, hexagonal prism, dodecagonal prism, icosagonal prism).

Figure 2A:
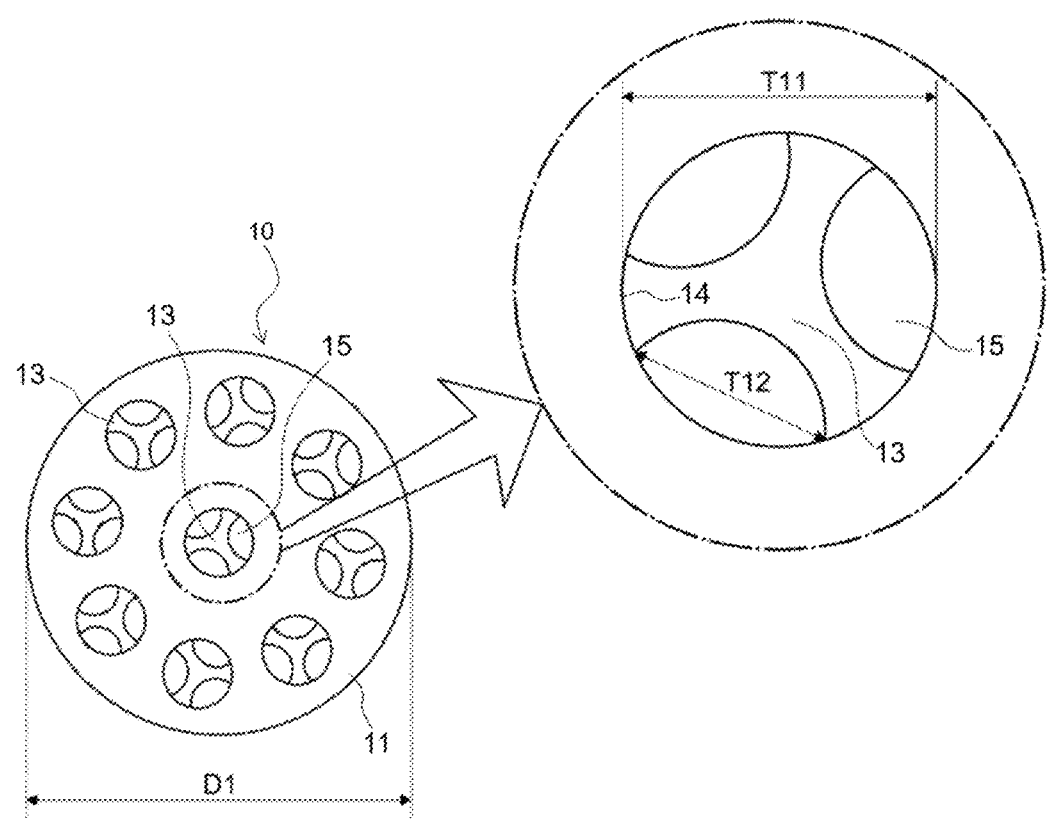
FIG. 2A is a schematic view of one example of the hydrocarbon synthesis catalyst of the present invention, viewed from one end surface. An enlarged view is also shown for portions surrounded by dashed-dotted lines.
Figure 2B:
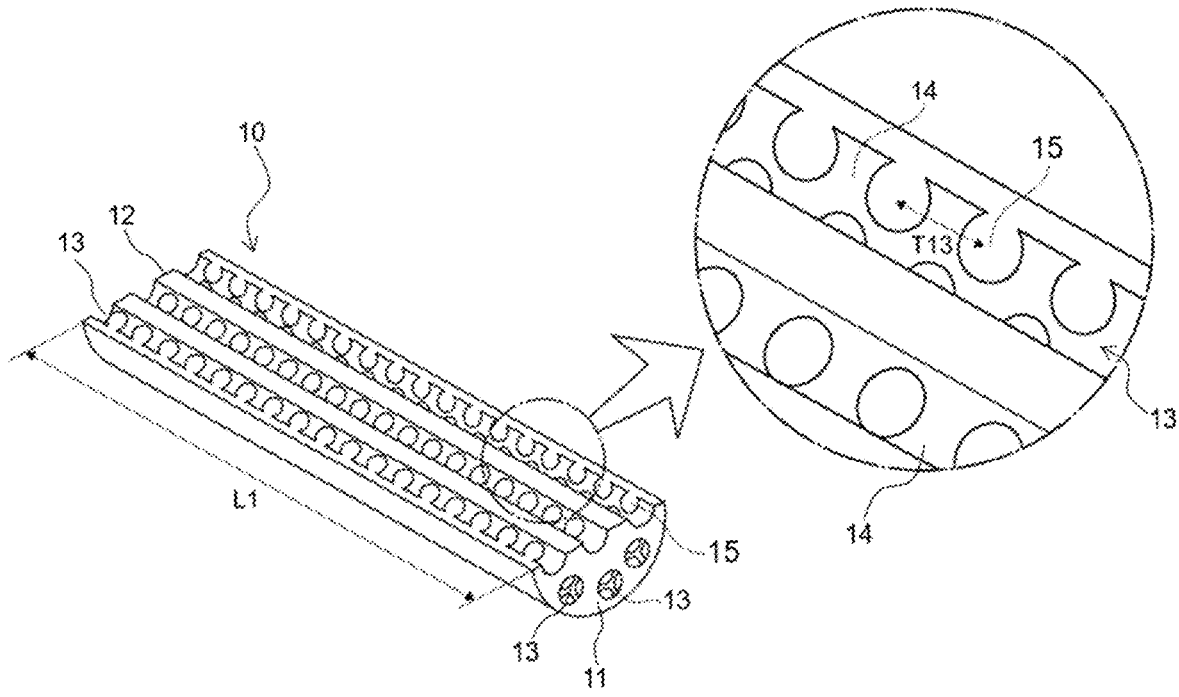
FIG. 2B is a schematic cross-sectional perspective view of the hydrocarbon synthesis catalyst shown in FIG. 2A cut along a plane passing through the central axis and parallel to the direction in which the flow paths extend. An enlarged view is also shown for portions surrounded by dashed-dotted lines.

One or more of protrusions 15 may be provided on the way of the flow paths 13. Referring to FIGS. 2A and 2B, the shape of the protrusion 15 is not particularly limited, but may be substantially hemispherical, substantially trapezoidal in cross-section, substantially V-wing shaped, substantially triangular in cross-section, and the like. Specific embodiments of the protrusion are as described in Japanese Patent Application Publication No. 2021-186724, the entire content of which is incorporated herein by reference. The illustrated hydrocarbon synthesis catalyst, when viewed from one end surface, has one flow path 13 in the center and a plurality of flow paths 13 at equal intervals around the flow path 13 in the center. The number of flow paths 13 is not particularly limited, and may be appropriately set according to the amount of raw material gas to be processed. For example, the number can be 1 to 11 (in FIG. 2A, the number is 9). In addition, a plurality of substantially hemispherical protrusions 15 are provided on the surface 14 of the flow paths 13. The plurality of protrusions 15 are regularly arranged at intervals in the circumferential direction of the flow paths 13 and in the extending direction of the flow paths 13. In the illustrated hydrocarbon synthesis catalyst, three protrusions 15 are provided at equal intervals in the circumferential direction of the flow paths 13.

Although not limited, each flow path may have an opening area of 0.5 to 3.5 $mm^2$, preferably 1.0 to 2.5 $mm^2$, and more preferably 1.5 to 2.0 $mm^2$ (excluding protrusions, if any) in a cross-section perpendicular to the direction in which the flow path extends. There is no particular restriction on the shape of the opening in the cross-section perpendicular to the direction in which the flow path extends, and it may be circular or polygonal.

The BET specific surface area of the surface of the one or more flow paths is preferably 5 to 15 $m^2$/g, more preferably 5 to 10 $m^2$/g, even more preferably 5 to 7 $m^2$/g. In the shaped hydrocarbon synthesis catalyst, the BET specific surface area of the surface of one or more flow paths was measured under the following conditions in the Examples.

Device: Multi-specimen high-performance specific surface area/pore size distribution measuring device (3Flex-2MP manufactured by Micromeritics Instrument Corporation, USA)

Measurement method: gas adsorption method by constant volume method

Gas used: Nitrogen

Pretreatment: degassing the sample at 250° C. for 10 hours under vacuum conditions Sample preparation: the shaped article is cut with a fine cutter such that the length of the flow paths is 3 mm. Next, four divided samples are obtained by two cutting lines perpendicular to each other that intersect at the center of gravity of a cross-section perpendicular to the length direction of the flow paths of the shaped article such that at least one or more flow paths are included (if the shaped article is cylindrical, a quadrant-shaped sample is obtained.)

The BET specific surface area of the sample is determined. Then, this is multiplied by the ratio of the area of the flow path surface to the total geometric surface area of the sample (the sum of the areas of the end surface, side surface, and flow path surface), and the result is defined as the measured value of the BET specific surface area of the surface of the flow path of the sample. The BET specific surface area of the surface of the flow path is measured in the same manner for the remaining three samples. Then, the average value of the measured values of the four samples is taken as the BET specific surface area of the surface of the one or more flow paths of the shaped article.

In addition, when the number of the flow paths is few, each sample may not necessarily include one or more flow paths.

(2. Method for Manufacturing Hydrocarbon Synthesis Catalyst)

According to one embodiment of the invention, a method for manufacturing a hydrocarbon synthesis catalyst is provided. For example, if the hydrocarbon synthesis catalyst is provided in the form of powder, the method for manufacturing the hydrocarbon synthesis catalyst in one embodiment comprises: a step A1 of preparing a Fe—Cr alloy powder comprising 50 to 90% by mass of Fe, 10 to 20% by mass of Cr, and 0 to 20% by mass of Ni; a step A2 of impregnating the powder with Na to obtain a Na-impregnated powder; and a step A3 of firing the Na-impregnated powder in an oxygen-containing atmosphere at 380 to 880° C.

(Step A1)

In the step A1, Fe—Cr alloy powder containing 50 to 90% by mass of Fe, 10 to 20% by mass of Cr, and 0 to 20% by mass of Ni is prepared. The Fe concentration in the Fe—Cr alloy is preferably 50 to 90% by mass, more preferably 50 to 80% by mass, and even more preferably 55 to 75% by mass. The Cr concentration in the Fe—Cr alloy is preferably 10 to 20% by mass, more preferably 12 to 18% by mass, and even more preferably 14 to 18% by mass. The Ni concentration in the Fe—Cr alloy is preferably 0 to 20% by mass, more preferably 1 to 20% by mass, more preferably 3 to 15% by mass, even more preferably 3 to 10% by mass, and even more preferably 3 to 5% by mass.

The total concentration of Fe, Cr and Ni in the Fe—Cr alloy is preferably 80% by mass or more, more preferably 85% by mass or more, and even more preferably 90% by mass or more. There is no particular upper limit to the total concentration of Fe, Cr and Ni, and it may be 100% by mass. However, since impurity elements and additive elements may be included, the total concentration is usually 98% by mass or less.

Among the above elements, Ni is a hydrogenation catalyst that easily produces methane, and affects the selectivity to hydrocarbons with 5 or more carbon atoms. Therefore, it is important to adjust it. That is, the lower the Ni concentration in the Fe—Cr alloy is, the higher the selectivity to hydrocarbons having 5 or more carbon atoms is, which is desirable. Ni may not be contained, but it is desirable to contain a small amount of Ni from the viewpoint of the mechanical strength of the catalyst.

The Fe—Cr alloy may contain elements other than Fe, Cr and Ni. In one embodiment, in the Fe—Cr alloy, Si may be contained in an amount of 0 to 5.0% by mass, for example, 0.5 to 3.0% by mass, Al may be contained in an amount of 0 to 1.0% by mass, for example, 0 to 0.5% by mass, Mn may be contained in an amount of 0 to 2.0% by mass, for example, 0.5 to 1.5% by mass, Cu may be contained in an amount of 0 to 5.0% by mass, for example, 3.0 to 5.0% by mass, Nb may be contained in an amount of 0 to 1.0% by mass, for example, 0.1 to 0.3% by mass, and Mo may be contained in an amount of 0 to 3% by mass, for example, 0.2 to 2.0% by mass. The Fe—Cr alloy may contain elements other than Fe, Cr, Ni, Si, Al, Mn, Cu, Nb and Mo as additive elements, but the total content of these elements is usually 5% by mass or less, typically 2% by mass or less, and more typically 1% by mass or less. In addition, the Fe—Cr alloy may contain unavoidable impurities.

Preferred specific examples of the Fe—Cr alloy include stainless steels such as SUS630 (JIS G4304-2012) and SUS420J2 (JIS G4303: 2021).

When the particle size distribution of the Fe—Cr alloy powder is analyzed by a laser diffraction/scattering method, the volume-based median diameter (D50) is preferably 5 to 20 μm, more preferably 10 to 20 μm, and even more preferably 10 to 17 μm. In addition, when the particle size distribution of the Fe—Cr alloy powder is analyzed by a laser diffraction/scattering method, the volume-based cumulative 90% diameter (D90) is preferably 5 to 40 μm, more preferably 10 to 35 μm, and even more preferably 15 to 30 μm.

The BET specific surface area of the Fe—Cr alloy powder is preferably 10 to 20 $m^2/g$, preferably 15 to 17 $m^2/g$. The BET specific surface area of the Fe—Cr alloy powder was measured under the following conditions in the Examples.

Device: Multi-specimen high-performance specific surface area/pore size distribution measuring device (3Flex-2MP manufactured by Micromeritics Instrument Corporation, USA)

Measurement method: gas adsorption method by constant volume method

Gas used: nitrogen

Pretreatment: degassing the sample at 250° C. for 10 hours under vacuum conditions Sample measurement amount: about 0.1 g (Step A2)

In the step A2, Na-impregnated powder is obtained by impregnating Fe—Cr alloy powder with Na. The method for impregnating the powder with Na is not limited, and examples include a method of contacting the powder with an aqueous solution of sodium salt such as sodium nitrate ($NaNO_3$), sodium carbonate ($Na_2CO_3$), organic sodium (for example, sodium phenoxide, sodium methoxide, and sodium methacrylate). The sodium salt to be used is preferably one from which the anion is removed by decomposition during firing. As a method of contacting the powder with the aqueous solution of sodium salt, a method of immersing the powder in the aqueous solution of sodium salt, a method of spraying and/or dispensing the aqueous solution of sodium salt on the powder, and a method of pouring the aqueous solution of sodium salt over the powder are mentioned for example. Among these, the method of pouring the aqueous solution of sodium salt over the powder is preferred due to its good operability and convenience, easy recovery of wet powder, and easy removal of contaminating anions in the post-process because only the required amount is adsorbed. As a specific example of the pouring method, there is a method in which the powder is placed on a mesh funnel and the aqueous solution of sodium salt is poured over the powder. The filtrate may be repeatedly poured over. Moreover, when contacting the aqueous solution of sodium salt with the powder, the powder may be stirred.

The Na concentration in the aqueous solution of sodium salt is not limited, but is preferably 0.0004 to 0.01 mol/L, more preferably 0.0004 to 0.008 mol/L, and even more preferably 0.0004 to 0.004 mol/L. The temperature of the aqueous solution of the sodium salt can be, but is not limited to, for example, 5 to 40° C., and typically 10 to 30° C.

After Na impregnation, it is preferable to dry with hot gas in air. The temperature during hot gas drying can be, for example, 50 to 100° C., and typically 50 to 70° C.

(Step A3)

In the step A3, the Na-impregnated powder obtained in the step A2 is fired in an oxygen-containing atmosphere at 380 to 880° C. If the temperature of the oxygen atmosphere during firing is excessively high, Na may vaporize and desorb. However, by performing the pickling treatment, which will be described later, the stable oxide film on the surface is removed, so low-temperature firing is possible. The lower limit of the oxygen-containing atmosphere temperature during firing is preferably 380° C. or higher, more preferably 400° C. or higher, and even more preferably 500° C. or higher, from the viewpoint of promoting the formation of iron oxides and promoting the decomposition of sodium salts. The upper limit of the oxygen-containing atmosphere temperature during firing is preferably 880° C. or lower, more preferably 800° C. or lower, and even more preferably 700° C. or lower, in order to suppress Na from evaporating and desorbing. The oxygen-containing atmosphere is not particularly limited as long as iron oxide can be generated, and examples include an oxygen atmosphere, an air atmosphere, and a mixed gas atmosphere of oxygen and an inert gas (Ar, He, and the like). From the viewpoint of promoting the formation of iron oxides, the firing time at the oxygen-containing atmosphere temperature is preferably 10 to 40 hours, more preferably 15 to 30 hours, and even more preferably 20 to 30 hours.

Further, the temperature rising rate can be, for example, 1 to 10° C./min, typically 2 to 5° C./min. There are no particular restrictions on the cooling rate, and for example, natural cooling may be performed.

(Step A4)

Between the steps A1 and A2, it is preferable to carry out a step A4 of pickling the Fe—Cr alloy powder. By performing the step A4, the surface area of the powder can be increased. As a result, more Fe atoms are exposed, and contact with oxygen molecules is promoted during firing, and iron oxides can be sufficiently produced even at a relatively low temperature. The acid used for pickling is not limited, but an acidic aqueous solution having a pH of 0.1 or less is preferable. Acidic aqueous solutions include hydrochloric acid, nitric acid, or mixtures of two or more thereof. Among these, a mixture of hydrochloric acid and nitric acid is preferred, a mixture of concentrated hydrochloric acid (6 to 12 mol/L) and concentrated nitric acid (7 to 13 mol/L) is more preferred, a mixture of concentrated hydrochloric acid (10 to 12 mol/L) and concentrated nitric acid (11 to 13 mol/L) in a volume ratio of 2.5:1 to 3.5:1 is even more preferred, and aqua regia is more preferred, because they are highly corrosive to metals, the oxide film can be easily removed, and they are possible to ionize metal atoms with poor reactivity, so the temperature conditions in the firing process can be relaxed.

Examples of the method for pickling the Fe—Cr alloy powder include a method of immersing the powder in an acidic aqueous solution, a method of spraying and/or dispensing the acidic aqueous solution on the powder, and a method of pouring the acidic aqueous solution over the powder, and the like. Among these, the pouring method is preferable because wet powder can be easily recovered and the amount of the acid solution can be suppressed to a small amount. As a specific example of the pouring method, there is a method in which the powder is placed on a mesh funnel and the acidic aqueous solution is poured over the powder. The filtrate may be repeatedly poured over. Moreover, when contacting the acidic aqueous solution with the Fe—Cr alloy powder, the powder may be stirred.

The temperature of the acidic aqueous solution is not limited, but can be, for example, 5 to 40° C., typically 10 to 30° C. After pickling, it is preferable to dry with hot gas in air. The temperature during hot gas drying can be, for example, 50 to 100° C., and typically to 70° C.

Further, when the hydrocarbon synthesis catalyst is provided in the form of a shaped article comprising one or more flow paths penetrating from one end surface to the other end surface, wherein a surface of the flow paths constitutes the surface of the hydrocarbon synthesis catalyst to be brought into contact with a raw material gas, the method for manufacturing a hydrocarbon synthesis catalyst according to one embodiment comprises: a step B1 of preparing a Fe—Cr alloy powder comprising 50 to 90% by mass of Fe, 10 to 20% by mass of Cr, and 0 to 20% by mass of Ni; a step B2 of shaping the powder using an additive manufacturing method into a shaped article comprising one or more flow paths penetrating from one end surface to the other end surface; a step B3 of impregnating a surface of the one or more flow paths of the shaped article with Na to obtain a Na-impregnated shaped article; and a step B4 of firing the Na-impregnated shaped article in an oxygen-containing atmosphere at 380 to 880° C.

(Step B1)

Since the step B1 is the same as the step A1 described above, description thereof is omitted.

(Step B2)

In the step B2, the Fe—Cr alloy powder is shaped with an additive manufacturing method into a shaped article having one or more flow paths penetrating from one end surface to the other end surface. The specific structural examples of the shaped article are as described above. There are no particular restrictions on the method of shaping the Fe—Cr alloy powder with the additive manufacturing method, and examples include a powder bed fusion method (powder bed method) and a directed energy deposition method (powder deposition method).

An example of the shaping procedure by the powder bed fusion method is shown below.

(1) From a raw material supply pallet containing Fe—Cr alloy powder, the powder is supplied onto a shaping stage and spread thereon. At this time, the powder spread on the shaping stage is equivalent to one layer to be shaped.

(2) Next, based on a three-dimensional CAD or CG data, an electron beam or a laser beam is irradiated to melt/solidify, or sinter the powder spread on the shaping stage to form a single shaped layer.

(3) Next, the shaping stage is lowered. At this time, the shaping stage is lowered such that the powder to be spread on the shaping stage is equivalent to one layer to be shaped.

(4) By repeating the above operations (1) to (3), a shaped article having a desired shape is obtained.

The BET specific surface area of the surface of one or more flow paths of the shaped article obtained in the step B2 is preferably 5 to 10 m²/g, preferably 6 to 8 m²/g. The BET specific surface area of the surface of one or more flow paths of the shaped article was measured under the following conditions in the Examples.

Device: Multi-specimen high-performance specific surface area/pore size distribution measuring device (3Flex-2MP manufactured by Micromeritics Instrument Corporation, USA)

Measurement method: gas adsorption method by constant volume method

Gas used: Nitrogen

Pretreatment: degassing the sample at 250° C. for 10 hours under vacuum conditions Sample preparation: the shaped article is cut with a fine cutter such that the length of the flow paths is 3 mm. Next, four divided samples are obtained by two cutting lines perpendicular to each other that intersect at the center of gravity of a cross-section perpendicular to the length direction of the flow paths of the shaped article such that at least one flow path is included (if the shaped article is cylindrical, a quadrant-shaped sample is obtained.)

The BET specific surface area of the sample is determined. Then, this is multiplied by the ratio of the area of the flow path surface to the total geometric surface area of the sample (the sum of the areas of the end surface, side surface, and flow path surface), and the result is defined as the measured value of the BET specific surface area of the surface of the flow path of the sample. The BET specific surface area of the surface of the flow path is measured in the same manner for the remaining three samples. Then, the average value of the measured values of the four samples is taken as the BET specific surface area of the surface of the one or more flow paths of the shaped article.

In addition, when the number of the flow paths is few, each sample may not necessarily include one or more flow paths.

(Step B3)

In the step B3, a Na-impregnated shaped article is obtained by impregnating the surface of the one or more flow paths of the shaped article obtained in the step B2 with Na. The method for impregnating the surface of the one or more flow paths with Na is not limited, and examples include a method of contacting the surface of the one or more flow paths with an aqueous solution of a sodium salt such as sodium nitrate ($NaNO_3$), sodium carbonate ($Na_2CO_3$), organic sodium (for example, sodium phenoxide, sodium methoxide, and sodium methacrylate). As a method of contacting the surface of the one or more flow paths with the aqueous solution of sodium salt, a method of immersing the shaped article in the aqueous solution of sodium salt, and a method of pouring the aqueous solution of sodium salt into the one or more flow paths are mentioned for example. Among these, the method of pouring the aqueous solution of sodium salt into the one or more flow paths is preferred due to its good operability and convenience, and easy removal of contaminating anions in the post-process because only the required amount is adsorbed. The aqueous solution of sodium salt that has flowed out from the shaped article may be poured repeatedly.

The Na concentration in the aqueous solution of sodium salt is not limited, but is preferably 0.1 to 3.0 mol/L, more preferably 0.1 to 1.0 mol/L, and even more preferably 0.1 to 0.5 mol/L. The temperature of the aqueous solution of the sodium salt can be, but is not limited to, for example 5 to 40° C., and typically 10 to 30° C.

Moreover, after Na impregnation, it is preferable to dry with hot gas in air. The temperature during hot gas drying can be, for example, 50 to 100° C., and typically 50 to 70° C.

(Step B4)

In the step B4, the Na-impregnated shaped article obtained in the step B3 is fired in an oxygen-containing atmosphere at 380 to 880° C. If the temperature of the oxygen atmosphere during firing is excessively high, Na may vaporize and desorb. However, by performing the pickling treatment, which will be described later, the stable oxide film on the surface is removed, so low-temperature firing is possible. The lower limit of the oxygen-containing atmosphere temperature during firing is preferably 380° C. or higher, more preferably 400° C. or higher, and even more preferably 500° C. or higher, from the viewpoint of promoting the formation of iron oxides and promoting the decomposition of sodium salts. The upper limit of the oxygen-containing atmosphere temperature during firing is preferably 880° C. or lower, more preferably 800° C. or lower, and even more preferably 700° C. or lower, in order to suppress Na from evaporating and desorbing. The oxygen-containing atmosphere is not particularly limited as long as iron oxide can be generated, and examples include an oxygen atmosphere, an air atmosphere, and a mixed gas atmosphere of oxygen and an inert gas (Ar, He, and the like). From the viewpoint of promoting the formation of iron oxides, the firing time at the oxygen-containing atmosphere temperature is preferably 10 to 40 hours, more preferably 15 to 30 hours, and even more preferably 20 to 30 hours.

Further, the temperature rising rate can be, for example, 1 to 10° C./min, typically 2 to 5° C./min. There are no particular restrictions on the cooling rate, and for example, natural cooling may be performed.

(Step B5)

Between the steps B2 and B3, it is preferable to carry out a step B5 of pickling the surface of the one or more flow paths of the shaped article. By performing the step B5, the surface area of the one or more flow paths can be increased. The acid used for pickling is not limited, but an acidic aqueous solution having a pH of 0.1 or less is preferable. Acidic aqueous solutions include hydrochloric acid, nitric acid, or mixtures of two or more thereof. Among these, a mixture of hydrochloric acid and nitric acid is preferred, a mixture of concentrated hydrochloric acid (6 to 12 mol/L) and concentrated nitric acid (7 to 13 mol/L) is more preferred, a mixture of concentrated hydrochloric acid (10 to 12 mol/L) and concentrated nitric acid (11 to 13 mol/L) in a volume ratio of 2.5:1 to 3.5:1 is even more preferred, and aqua regia is more preferred, because they are highly corrosive to metals, the oxide film can be easily removed, and they are possible to ionize metal atoms with poor reactivity, so the temperature conditions in the firing process can be relaxed.

Examples of the method for pickling the one or more flow paths include a method of immersing the shaped article in an acidic aqueous solution, and a method of pouring the acidic aqueous solution into the one or more flow paths, and the like. Among these, the method of pouring an acidic aqueous sodium salt solution into the one or more flow paths is preferable due to good operability and convenience, and the waste liquid is easy to collect. The acidic aqueous solution that has flowed out from the shaped article may be poured repeatedly.

In addition, the temperature of the acidic aqueous solution is not limited, but can be, for example, 5 to 40° C., typically 10 to 30° C. After pickling, it is preferable to dry with hot gas in air. The temperature during hot gas drying can be, for example, 50 to 100° C., and typically 50 to 70° C.

(3. Method for Synthesizing Hydrocarbons)

According to one embodiment of the present invention, there is provided a method for synthesizing hydrocarbons, comprising contacting a raw material gas comprising hydrogen and carbon dioxide with the surface of the above-described hydrocarbon synthesis catalyst to be brought into contact with the raw material gas, thereby reacting the raw material gas. By using the hydrocarbon synthesis catalyst described above, it is possible to synthesize hydrocarbons having 5 or more carbon atoms with high selectivity.

The selectivity to hydrocarbons having 5 or more carbon atoms can be, for example, 20% by volume or more, preferably 25% by volume or more, more preferably 30% by volume or more, even more preferably 35% by volume or more, even more preferably 40% by volume or more, even more preferably 45% by volume or more, and can be typically in the range of 20 to 60% by volume. A method for calculating the selectivity to hydrocarbons having 5 or more carbon atoms will be described in Examples below.

While not intending to limit the invention by any theory, it is speculated that a raw material gas containing hydrogen and carbon dioxide is converted to hydrocarbons by the following two-step reaction.

Reverse water gas shift reaction: $CO_2 + H_2 \rightarrow CO + H_2O$ (1)

FT (Fischer-Tropsch) reaction: $nCO + 2nH_2 \rightarrow (CH2)_n + nH_2O$ (2)

Although the molar ratio of hydrogen ($H_2$) and carbon dioxide ($CO_2$) contained in the raw material gas is not limited, the amount of $H_2$ used is more than the molar ratio used for hydrocarbon synthesis (FT reaction) as $H_2$ is required when reducing $CO_2$ to CO. In addition, because of a reversible reaction, the reaction is likely to shift towards hydrocarbon production as the amount of reactant $H_2$ is increased. Therefore, the $H_2$:$CO_2$ ratio is preferably 2:1 to 4:1, more preferably 2.5:1 to 4:1, even more preferably 3:1 to 4:1.

The raw material gas may contain gas components other than hydrogen and carbon dioxide. For example, gas components such as carbon monoxide, water vapor, methane, argon, and helium may be contained in a total amount of 1 to 10 mol %, or 1 to 5 mol %. However, gas components other than hydrogen and carbon dioxide are unnecessary in the raw material gas, so the total amount of gas components other than hydrogen and carbon dioxide contained in the raw material gas can be 10 mol % or less, and 7 mol % or less, more preferably 5 mol % or less.

There are no particular restrictions on the method of bringing the raw material gas into contact with the surface of the hydrocarbon synthesis catalyst to be brought into contact with the raw material gas. For example, when the hydrocarbon synthesis catalyst is in the form of powder, there is a method in which a fixed or fluidized catalyst layer filled with the hydrocarbon synthesis catalyst is provided on the way of the route of the raw material gas, and the raw material gas is allowed to pass through the catalyst layer. In addition, when the hydrocarbon synthesis catalyst is a shaped article having one or more flow paths penetrating from one end surface to the other end surface, there is a method in which a hydrocarbon synthesis catalyst is installed on the way of the route of the raw material gas, and the raw material gas is passed through the one or more flow paths. A plurality of shaped articles of hydrocarbon synthesis catalysts may be arranged in parallel and/or in series according to the flow rate of the raw material gas.

When the raw material gas is reacted, the catalyst is preferably heated to 300 to 500° C., more preferably 320 to 450° C., and even more preferably 360 to 400° C., in order to increase the reaction rate.

When the raw material gas is reacted, it is preferable to pressurize the raw material gas to 1 to 5 MPa (gauge pressure), more preferably 2 to 4 MPa (gauge pressure), in order to increase the reaction rate.

The catalyst passing time of the raw material gas is preferably 1.0 to 15.0 s, more preferably 1.5 to 12.0 s, and even more preferably 2.0 to 10.0 s, in order to increase the reaction rate. For example, when the hydrocarbon synthesis catalyst is in the form of powder, and when adopting a method in which a fixed or fluidized catalyst layer filled with the hydrocarbon synthesis catalyst is provided on the way of the route of the raw material gas and the raw material gas is allowed to pass through the catalyst layer, the catalyst passing time of the raw material gas is the time from when the raw material gas flows into the catalyst layer to the time when the reaction product flows out of the catalyst layer, and is expressed by the following formula.

$$\text{Catalyst passing time} = \frac{\text{Height of catalyst filled bed (cm)} \times \text{Cross-sectional area of reactor}\left(\text{cm}^2\right)}{\text{Raw material gas supply rate (mL/min)}} \times 60 \text{ s/min}$$

Further, when the hydrocarbon synthesis catalyst is a shaped article having one or more flow paths penetrating from one end surface to the other end surface, and when adopting a method in which a hydrocarbon synthesis catalyst is installed on the way of the route of the raw material gas and the raw material gas is passed through the one or more flow paths, The catalyst passing time of the raw material gas is the time from when the raw material gas flows into the flow path from one end surface to the time when the reaction product flows out from the other end surface, and is expressed by the following formula.

$$\text{Catalyst passing time} = \frac{\text{Volume of flow path 13}\left(\text{cm}^3\right) \times \text{Number of flow path 13}}{\text{Raw material gas supply rate (mL/min)}} \times 60 \text{ s/min}$$

When two or more shaped articles are arranged in series, the catalyst passing time is represented by the sum of the catalyst passing time of each of the two or more shaped articles.

Before reacting the raw material gas, it is preferable to contact the hydrogen gas with the surface of the hydrocarbon synthesis catalyst to be brought into contact with the raw material gas to perform a pretreatment of reducing the surface. By performing the pretreatment, the iron oxide present on the surface is partially reduced and oxygen defects are introduced on the surface. The introduction of oxygen defects is preferable as it strengthens the momentum of surplus electrons existing in oxygen lattice vacancies to strip off oxygen in $CO_2$. This is because the binding force between the catalyst surface and the $CO_2$ molecules is strengthened, and the probability of the $CO_2$ molecules coming into contact with the catalyst surface increases, making the reaction easier to occur.

There are no particular restrictions on the method of bringing the hydrogen gas into contact with the surface of the hydrocarbon synthesis catalyst to be brought into contact with the raw material gas. For example, when the hydrocarbon synthesis catalyst is in the form of powder, there is a method in which a fixed or fluidized catalyst layer filled with the hydrocarbon synthesis catalyst is provided on the way of the route of the hydrogen gas, and the hydrogen gas is allowed to pass through the catalyst layer. In addition, when the hydrocarbon synthesis catalyst is a shaped article having one or more flow paths penetrating from one end surface to the other end surface, there is a method in which a hydrocarbon synthesis catalyst is installed on the way of the route of the hydrogen gas, and the hydrogen gas is passed through the one or more flow paths.

In order to increase the reaction rate during the pretreatment, the hydrogen gas is preferably heated to 300 to 700° C., more preferably 300 to 600° C., and even more preferably 300 to 500° C.

The hydrogen gas flow time for the pretreatment is preferably 4 to 12 hours, more preferably 6 to 12 hours, and even more preferably 8 to 12 hours, in order to introduce sufficient oxygen defects.

EXAMPLES

The following examples of the invention are provided for a better understanding of the present invention and its advantages. However, it is not intended that the invention be limited.
[I. Regarding the Influence of Ni Content and Catalyst Form on Catalyst Performance]
<A. Manufacture of Catalyst in the Form of Powder>

Example 1

Commercially available SUS630 powder (containing Fe: 73.97% by mass, Cr: 16.39% by mass, Ni: 4.8% by mass, Cu: 3.57% by mass, Nb: 0.22% by mass, C: 0.028% by mass, Si: 0.45% by mass, Mn: 0.56% by mass, and unavoidable impurities) was prepared as a catalyst raw material.

For a sample of the powder, the volume-based median diameter (D50) and D90 were measured using a laser diffraction/scattering particle size distribution analyzer (MT3200 manufactured by Microtrac).

For a sample of the powder, the BET specific surface area was measured under the above-described measurement conditions.

For a sample of the powder, the surface was analyzed by X-ray diffraction (XRD) under the measurement conditions described above, and the ratio ($I_2/I_1$) in which $I_1$ is the peak area in the range of $2\theta = 44°$ to $45°$ representative of Fe—Cr alloy, and $I_2$ is the peak area in the range of $2\theta = 35°$ to $36°$ representative of $Fe_2O_3$), and the ratio ($I_3/I_1$) (in which $I_1$ is the peak area in the range of $2\theta = 44°$ to $45°$ representative of Fe—Cr alloy, and $I_3$ is the peak area in the range of $2\theta = 30°$ to $31°$ representative of $FeCr_2O_4$) were calculated.
The results are shown in Table 1.

A pickling solution (pH=0.1 or less) was prepared by mixing hydrochloric acid (8.7 mol/L) and nitric acid (3.3 mol/L) at a volume ratio of hydrochloric acid:nitric acid=3:1. 200 mL of this pickling solution (20° C.) was poured over 7 to 8 g of the above-described powder which was placed on a mesh funnel with a pipette. The filtrate was poured over the powder several times. The pickled powder was dried with hot air for 24 hours in a drying oven at 60° C. in communication with the atmosphere.

Then, the powder after drying with hot air was placed on a mesh funnel, and 200 mL of a 0.004 mol/L sodium nitrate aqueous solution (20° C.) was poured over the powder with a pipette for Na impregnation. The filtrate was poured over the powder several times. The Na-impregnated powder was dried with hot air for 24 hours in a drying oven at 60° C. in communication with the atmosphere.

The obtained Na-impregnated powder was placed in an alumina crucible, heated in a muffle furnace at a temperature elevation rate of 2° C./min, fired in air at 550° C. for 24 hours, and then allowed to cool naturally. The sintered body taken out from the alumina crucible was pulverized with a pressure apparatus and further sieved to manufacture a powder catalyst having a particle size distribution with a median diameter as shown in Table 1.

For a sample of the powder catalyst, the volume-based median diameter (D50) was measured using the laser diffraction/scattering method under the above-described measurement conditions.

For a sample of the powder catalyst, the BET specific surface area was measured under the above-described measurement conditions.

For a sample of the powder catalyst, the surface was analyzed by X-ray diffraction (XRD) under the measurement conditions described above, and $I_2/I_1$ and $I_3/I_1$) were calculated.

For a sample of the powder catalyst, elemental analysis of the surface was performed by energy dispersive X-ray spectroscopy (SEM-EDX) under the measurement conditions described above.
The results are shown in Table 1.

Example 2

Commercially available SUS316L powder (containing Fe: 66.74% by mass, Cr: 17.11% by mass, Ni: 12.54% by mass, C: 0.018% by mass, Si: 0.81% by mass, Mn: 0.73% by mass, Mo: 2.04% by mass, and contains unavoidable impurities) was prepared as a catalyst raw material.

For a sample of the powder, the volume-based median diameter (D50) and D90 were measured using a laser diffraction/scattering particle size distribution analyzer (MT3200 manufactured by Microtrac).

A pickling solution (pH=0.1 or less) was prepared by mixing hydrochloric acid (8.7 mol/L) and nitric acid (3.3 mol/L) at a volume ratio of hydrochloric acid:nitric acid=3:1. 200 mL of this pickling solution (20° C.) was poured over 7 to 8 g of the above-described powder which was placed on a mesh funnel with a pipette. The filtrate was poured over the powder several times. The pickled powder was dried with hot air for 24 hours in an electric furnace at 60° C. in communication with the atmosphere.

Then, the powder after drying with hot air was placed on a mesh funnel, and 200 mL of a 0.004 mol/L sodium nitrate aqueous solution (20° C.) was poured over the powder with a pipette for Na impregnation. The filtrate was poured over the powder several times. The Na-impregnated powder was dried with hot air for 24 hours in an electric furnace at 60° C. in communication with the atmosphere.

The obtained Na-impregnated powder was placed in an alumina crucible, heated in a muffle furnace at a temperature elevation rate of 2° C./min, fired in air at 550° C. for 24 hours, and then allowed to cool naturally. The sintered body taken out from the alumina crucible was pulverized with a pressure apparatus and further sieved to manufacture a powder catalyst having a particle size distribution with a median diameter as shown in Table 1.

For a sample of the powder catalyst, the volume-based median diameter (D50) was measured using the laser diffraction/scattering method under the above-de-scribed measurement conditions.

For a sample of the powder catalyst, elemental analysis of the surface was performed by energy dispersive X-ray spectroscopy (SEM-EDX) under the measurement conditions described above.

The results are shown in Table 1.

<B. Manufacture of Shaped Catalyst>

Example 3

The same catalyst raw material (SUS630 powder) as in Example 1 was prepared. Next, by the powder bed fusion method using a metal 3D printer (Metal 3D printer tester manufactured by NISSEI ELECTRIC CO.) using a laser beam, three-dimensional shaping was performed by repeating melting and solidification of the catalyst raw material in a nitrogen atmosphere, thereby obtaining a cylindrical shaped article having a plurality of flow paths penetrating from one end surface to the other end surface. The BET specific surface area of the flow paths of the obtained sample of the shaped article was measured under the measurement conditions described above. In addition, the surface of the flow paths of the sample of the shaped article was analyzed by the X-ray diffraction method (XRD) under the measurement conditions described above, and $I_2/I_1$ and $I_3/I_1$ were calculated. The results are shown in Table 1.

A pickling solution (pH=0.1 or less) was prepared by mixing hydrochloric acid (12.0 mol/L) and nitric acid (13.0 mol/L) at a volume ratio of hydrochloric acid:nitric acid=3:1. 200 mL of this pickling solution (20° C.) was poured into each of the flow paths of the obtained shaped article as described above with a pipette for pickling. The acidic aqueous solution that flowed out from the shaped article was poured again for several times. After pickling, the shaped article was dried with hot air for 24 hours in an electric furnace at 60° C. in communication with the atmosphere.

Then, after drying with hot air, 200 mL of a 0.1 mol/L sodium nitrate aqueous solution (20° C.) was poured into each of the flow paths of the shaped article with a pipette for Na impregnation. The sodium nitrate aqueous solution that flowed out from the shaped article was poured again for several times. The Na-impregnated shaped article was dried with hot air for 24 hours in an electric furnace at 60° C. in communication with the atmosphere.

The obtained Na-impregnated shaped article was placed in an alumina crucible, heated in a muffle furnace at a temperature elevation rate of 2° C./min, fired in air at 550° C. for 24 hours, and then allowed to cool naturally, thereby manufacturing a shaped catalyst. The catalyst had a cylindrical shape with an outer diameter of 8 mm and a height of mm, and had nine flow paths extending in the height direction from one end surface to the other end surface. No protrusion was provided in each flow path. Each flow path had a circular shape opening in a cross-section perpendicular to the direction in which the flow path extended, and the opening area was 1.76 mm².

For a sample of the shaped catalyst, the BET specific surface area of the flow paths was measured under the measurement conditions described above.

For a sample of the shaped catalyst, the surface of the channel was analyzed by the X-ray diffraction method (XRD) under the measurement conditions described above, and $I_2/I_1$ and $I_3/I_1$ were calculated.

For a sample of the shaped catalyst, elemental analysis of the surface was performed by SEM-EDX under the measurement conditions described above.

The results are shown in Table 1.

Example 4

The same catalyst raw material (SUS316L powder) as in Example 2 was prepared. Next, by the powder bed fusion method using a metal 3D printer (Metal 3D printer tester manufactured by NISSEI ELECTRIC CO.) using a laser beam, three-dimensional shaping was performed by repeating melting and solidification of the catalyst raw material in a nitrogen atmosphere, thereby obtaining a cylindrical shaped article having a plurality of flow paths penetrating from one end surface to the other end surface. The results are shown in Table 1.

A pickling solution (pH=0.1 or less) was prepared by mixing hydrochloric acid (8.7 mol/L) and nitric acid (3.3 mol/L) at a volume ratio of hydrochloric acid:nitric acid=3:1. 200 mL of this pickling solution (20° C.) was poured into each of the flow paths of the obtained shaped article as described above with a pipette for pickling. The acidic aqueous solution that flowed out from the shaped article was poured over again for several times. After pickling, the shaped article was dried with hot air for 24 hours in an electric furnace at 60° C. in communication with the atmosphere.

Then, after drying with hot air, a 1.0 mol/L sodium nitrate aqueous solution (20° C.) was poured into each of the flow paths of the shaped article with a pipette for Na impregnation. The sodium nitrate aqueous solution that flowed out from the shaped article was poured again for several times. The Na-impregnated shaped article was dried with hot air for 24 hours in an electric furnace at 60° C. in communication with the atmosphere.

The obtained Na-impregnated shaped article was placed in an alumina crucible, heated in a muffle furnace at a temperature elevation rate of 2° C./min, fired in air at 550° C. for 24 hours, and then allowed to cool naturally, thereby manufacturing a shaped catalyst. The catalyst had a cylindrical shape with an outer diameter of 8 mm and a height of mm, and had nine flow paths extending in the height direction from one end surface to the other end surface. No protrusion was provided in each flow path. Each flow path had a circular shape opening in a cross-section perpendicular to the direction in which the flow path extended, and the opening area was 1.76 mm².

For a sample of the shaped catalyst, elemental analysis of the surface was performed by energy dispersive X-ray spectroscopy (SEM-EDX) under the measurement conditions described above.

The results are shown in Table 1.

<C. Synthesis of Hydrocarbons>

For the powder catalysts of Examples 1 and 2, a reactor was prepared by providing a catalyst layer in which 0.25 g of catalyst was fixedly filled in a stainless steel pipe having an inner diameter of 8 mm and a length of 60 mm and sandwiching it with quartz wool from above and below. Next, a gas supply pipe (made of stainless steel) was connected to the upstream side of the stainless steel pipe, and a gas outflow pipe (made of stainless steel) was connected to the downstream side to construct a hydrocarbon synthesis device having the configuration shown in FIG. 3. Incidentally, a thermocouple was inserted in the central position of the catalyst filled in the reactor.

Figure 3:
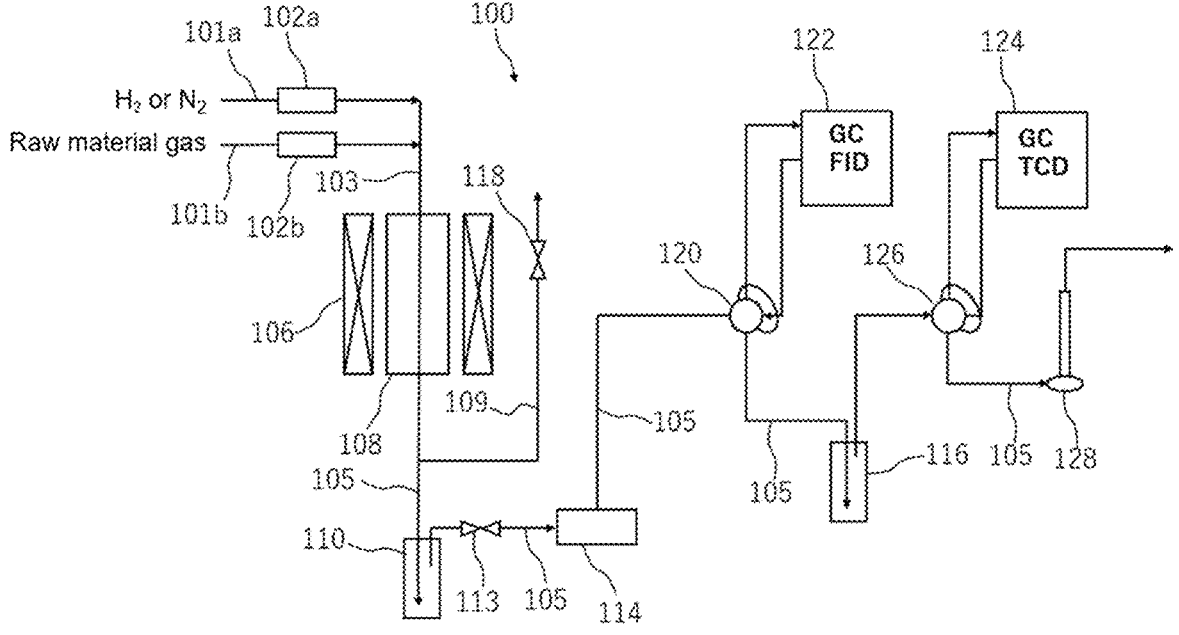
FIG. 3 is a schematic diagram for explaining the configuration of a hydrocarbon synthesis device used in the Examples.

Further, for the cylindrically shaped catalysts of Examples 3 and 4, the catalyst itself constituted the reactor. Therefore, a gas supply pipe (made of stainless steel) was connected to the upstream side of the catalyst and a gas outflow pipe (made of stainless steel) was connected to the downstream side of the catalyst to construct a hydrocarbon synthesis device configured as shown in FIG. 3. Incidentally, a thermocouple was inserted in the central position of the catalytic reactor.

The configuration of the hydrocarbon synthesis device 100 shown in FIG. 3 will be described. The hydrocarbon synthesis device 100 comprises a pipe 101*a* for $H_2$ and $N_2$ supply before hydrocarbon synthesis, a mass flow controller 102*a*, a raw material gas pipe 101*b*, a mass flow controller 102*b*, a gas supply pipe 103, a reactor 108, a heater 106, a gas outflow pipe 105, a first cooling container 110, a valve 113, a back pressure valve 114, a branch outflow pipe 109, a second cooling vessel 116, a valve 118, a 6-way valve 120, a GC-FID 122, a GC-TCD 124, a 6-way valve 126, and a soap film flow meter 128.

The mass flow controller 102*a* is installed in the pipe 101*a* for $H_2$ and $N_2$ supply before hydrocarbon synthesis, and it is possible to control the flow rate of $H_2$ and $N_2$. The mass flow controller 102*b* is installed in the raw material gas pipe 101*b*, and can control the flow rate of the raw material gas. The pipes 101*a* and 101*b* are connected to the gas supply pipe 103. After passing through the pipe 101*b*, the raw material gas passes through the gas supply pipe 103 and the reactor 108. It is also possible to flow $H_2$ or $N_2$ into the reactor 108 from the pipe 101*a* instead of the raw material gas. When the raw material gas passes through the reactor 108, it comes into contact with the catalyst in the reactor 108, causing a hydrocarbon synthesis reaction to produce reaction products such as hydrocarbons. The pressure of the raw material gas passing through the reactor 108 can be adjusted by valves 102*a*, 102*b*, valves 118 and 113. A heater 106 is installed so as to cover the outer periphery of the reactor 108, and the temperature inside the reactor 108 can be controlled. The reaction product flowing out of the reactor 108 flows through the gas outflow pipe 105 into the cooling container 110 made of pressure-resistant stainless steel whose outer peripheral side is ice-cooled, and the liquid component (organic component with a large number of carbon atoms) is recovered by gas-liquid separation. A residual organic component among the gas components flowing out from the cooling container 110 can be quantitatively analyzed in real time by the GC-FID 122 installed downstream. In addition, the low-molecular-weight components ($CO_2$, CO, $CH_4$, and carrier gas He) among the gas components flowing out of the cooling container 110 can be quantitatively analyzed by the GC-TCD 124 in real time after residual organic components are removed by the water trap 116. After that, the gas component is discharged out of the device. After completion of the test, the valve 113 is closed, the valve 118 is opened, and the internal pressure of the reactor is released through the branch outflow pipes 109 and 118.

Before starting the synthesis of hydrocarbons, the temperature of the catalyst was raised to 400° C. with a heater for 1 hour while flowing hydrogen gas into the reactor at 40 mL/min, and then reduction treatment was performed at normal pressure for 8 hours. After that, switching to a raw material gas (molar ratio $H_2$:$CO_2$=3:1) (containing 4% by volume of He as a carrier gas), the catalyst temperature was set to 380° C., and hydrocarbon synthesis was carried out for 8 hours at 3.0 MPa (gauge pressure) while continuously flowing the raw material gas into the reactor at 20 mL/min. The pressure was the value of the pressure gauge installed in the gas outflow pipe 105 between the cooling container 110 and the back pressure valve 114. At this time, the catalyst passing time of the raw material gas was 9.69 s for Examples 1 and 2, and 2.38 s for Examples 3 and 4.

The reaction product flowing out of the reactor was subjected to real-time component analysis according to the following procedure. First, as shown in FIG. 3, the reaction product was subjected to gas-liquid separation in the cooling container 110 which was maintained at 0° C. The gaseous component (organic components with a low carbon number) flowing out from the cooling container 110 was sent to the GC-FID 122 (Flame Ion Detector) (GC-2014AF manufactured by Shimadzu Corporation) for quantitative analysis. Further, as shown in FIG. 3, after the residual organic component was removed from the gas component flowing out from the cooling container 110 by the water trap 116, the gas components (low molecular weight components) were sent to the GC-TCD 124 (Thermal Conductivity Detector) (GC-2014AT manufactured by Shimadzu Corporation) for quantitative analysis. The liquid components (organic components with a large number of carbon atoms) collected in the cooling container 110 were quantitatively analyzed with an off-line GC-FID (Flame Ion Detector) (GC-2014AF manufactured by Shimadzu Corporation). By adding the two measurement results, the $CO_2$ conversion ratio, CO selectivity, and hydrocarbon selectivity were finally calculated by the following formulas. The results are shown in Table 1.

—$CO_2$ Conversion Ratio—

$$CO_2 \text{ conversion ratio (\%)}=(1-(\text{volume of } CO_2 \text{ flowing out from reactor})/(\text{volume of } CO_2 \text{ supplied to reactor}))\times100$$

—CO Selectivity—

$$CO \text{ selectivity (\%)}=(\text{volume of CO flowing out from reactor})/(\text{volume of decreased CO})\times100$$

—Hydrocarbon Selectivity—

$$CH_4 \text{ selectivity (\%)}=(\text{volume of } CH_4 \text{ flowing out from reactor})/(\text{volume of decreased } CO_2\text{–volume of CO flowing out from reactor})\times100$$

$$O_{2-4} \text{ selectivity (\%)}=(\text{volume of unsaturated hydrocarbon having 2 to 4 carbon atoms flowing out from reactor})/(\text{volume of decreased } CO_2\text{–volume of CO flowing out from reactor})\times100$$

$$C_{2-4} \text{ selectivity (\%)}=(\text{volume of saturated hydrocarbon having 2 to 4 carbon atoms flowing out from reactor})/(\text{volume of decreased } CO_2\text{–volume of CO flowing out from reactor})\times100$$

$$C_5^+ \text{ selectivity (\%)}=(\text{volume of hydrocarbon having 5 or more carbon atoms(sum of saturated and unsaturated)flowing out from reactor})/(\text{volume of decreased } CO_2\text{–volume of CO flowing out from reactor})\times100$$

TABLE 1

|  |  | Unit | Example 1 | Example 2 | Example 3 | Example 4 |
|---|---|---|---|---|---|---|
| Material | Catalyst raw material | — | SUS630 | SUS316L | SUS630 | SUS316L |
| Form | Catalyst (after pickling, Na impregnation, firing) | — | Powder | Powder | Shaped article | Shaped article |

TABLE 1-continued

| | | Unit | Example 1 | Example 2 | Example 3 | Example 4 |
|---|---|---|---|---|---|---|
| D90 | Catalyst raw material | μm | 25.85 | 18.99 | 25.85 | 18.99 |
| Median diameter (D50) | Catalyst raw material | μm | 16.44 | 11.00 | 16.44 | 11.00 |
| | Catalyst (after pickling, Na impregnation, firing) | μm | 355 to 850 | 355 to 850 | — | — |
| BET specific surface area | Catalyst raw material | m²/g | 15.33 | — | 5.36 | — |
| | Catalyst (after pickling, Na impregnation, firing) | m²/g | 16.03 | — | 6.47 | — |
| XRD ($I_2/I_1$) | Catalyst raw material | — | 0 | — | 0 | — |
| | Catalyst (after pickling, Na impregnation, firing) | — | 2.31 | — | 0.05 | — |
| XRD ($I_3/I_1$) | Catalyst raw material | — | 0 | — | 0 | — |
| | Catalyst (after pickling, Na impregnation, firing) | — | 0.09 | — | 0.13 | — |
| Elemental analysis of catalyst surface (SEM-EDX) | Fe | % by mass | 58.34 | 61.04 | 48.69 | 53.62 |
| | O | % by mass | 10.42 | 11.14 | 16.41 | 15.60 |
| | Na | % by mass | 0.18 | 0.06 | 1.31 | 3.10 |
| | Ni | % by mass | 8.17 | 3.22 | 1.87 | 6.38 |
| | C | % by mass | — | — | — | — |
| | Cr | % by mass | 19.06 | 18.75 | 20.73 | 12.55 |
| | Si | % by mass | 0.79 | 0.59 | 3.33 | 4.40 |
| | Al | % by mass | 0.38 | 0.37 | 1.59 | 0.60 |
| | Mn | % by mass | 0.81 | 1.13 | 1.86 | 2.03 |
| | Cu | % by mass | 0.23 | 3.34 | 2.58 | 0.40 |
| | Nb | % by mass | 0.11 | 0.22 | 0.84 | 0.19 |
| | Mo | % by mass | 1.51 | 0.14 | 0.76 | 1.13 |
| Catalyst performance | $CO_2$ conversion rate | % by volume | 48.1 | 48.0 | 30.5 | 32.1 |
| | CO selectivity | % by volume | 11.6 | 10.0 | 35.3 | 35.6 |
| | $CH_4$ selectivity | % by volume | 21.7 | 24.8 | 24.1 | 63.7 |
| | $O_{2-4}$ selectivity | % by volume | 16.0 | 16.8 | 15.4 | 4.7 |
| | $O_{2-4}$ selectivity | % by volume | 4.6 | 10.6 | 12.4 | 9.0 |
| | $C_5^+$ selectivity | % by volume | 57.7 | 47.8 | 48.1 | 22.6 |

Comparing Example 1 and Example 2, in which catalysts in the powder form were used, it was found that SUS630 with a lower Ni concentration had a lower $CH_4$ selectivity and an increased $C_5^+$ selectivity. Also, when comparing Example 3 and Example 4, in which shaped article of catalyst was used, similarly, it was found that SUS630 with a low Ni concentration had a lower $CH_4$ selectivity and an increased $C_5^+$ selectivity. From these results, it was confirmed that a reduction in Ni concentration has the effect of reducing $CH_4$ while promoting the formation of long-chain hydrocarbon compounds.

Comparing Example 1 and Example 3, which used SUS630 as a catalyst raw material, Example 1 using a catalyst in the form of powder was superior in catalytic performance. Further, when comparing Example 2 and Example 4, which used SUS316L as a catalyst raw material, Example 2 using a catalyst in the form of powder was superior in catalytic performance. From this result, it can be said that the catalyst in the form of powder is superior to the catalyst in the form of a shaped article in terms of catalytic performance. However, the catalyst in the form of a shaped article is advantageous in terms of downsizing of the reactor, quality stability, and convenience of recovery and regeneration. Therefore, practicability is higher for catalyst in the form of shaped article rather than that in the form of powder.

[II. Regarding Influence of Na Impregnation on Catalyst Performance]

<A. Manufacture of Shaped Catalyst>

Comparative Example 1

The same catalyst raw material (SUS316L powder) as in Example 4 was prepared. Next, by the powder bed fusion method using a metal 3D printer (Metal 3D printer tester manufactured by NISSEI ELECTRIC CO.) using a laser beam, three-dimensional shaping was performed by repeating melting and solidification of the catalyst raw material in a nitrogen atmosphere, thereby obtaining a cylindrical shaped article having a plurality of flow paths penetrating from one end surface to the other end surface. The shaped article had a cylindrical shape with an outer diameter of 8 mm and a height of 50 mm, and had nine flow paths extending in the height direction from one end surface to the other end surface. No protrusion was provided in each flow path. Each flow path had a circular shape opening in a cross-section perpendicular to the direction in which the flow path extended, and the opening area was 1.76 mm². In Comparative Example 1, the shaped article itself (without pickling or Na impregnation) was used as a catalyst.

Comparative Example 2

The same catalyst raw material (SUS630 powder) as in Example 3 was prepared. After that, a shaped catalyst (without pickling or Na impregnation) was manufactured by the same procedure as in Comparative Example 1.

Example 5

A shaped catalyst was manufactured in the same procedure as in Example 4, except that the concentration of sodium nitrate in the sodium nitrate aqueous solution used for Na impregnation was changed to 0.1 mol/L.

Example 6

A shaped catalyst was manufactured in the same procedure as in Example 4, except that the concentration of sodium nitrate in the sodium nitrate aqueous solution used for Na impregnation was changed to 0.3 mol/L.

Example 7

A shaped catalyst was manufactured in the same procedure as in Example 4, except that the concentration of sodium nitrate in the sodium nitrate aqueous solution used for Na impregnation was changed to 0.5 mol/L.

<B. Synthesis of Hydrocarbons>

Using each of the catalyst, a hydrocarbon synthesis device having the configuration shown in FIG. 3 was assembled in the same manner as in Example 4.

Before starting the synthesis of hydrocarbons, the temperature of the catalyst was raised to 400° C. with a heater for 1 hour while flowing hydrogen gas into the reactor at 40 mL/min, and then reduction treatment was performed at normal pressure for 8 hours. After that, switching to a raw material gas (molar ratio $H_2:CO_2=3:1$) (containing 4% by volume of He as a carrier gas), the catalyst temperature was set to 380° C., and hydrocarbon synthesis was carried out for 8 hours at 3.0 MPa (gauge pressure) while continuously flowing the raw material gas into the reactor at 20 mL/min. The pressure was the value of the pressure gauge installed in the gas outflow pipe 105 between the cooling container 110 and the back pressure valve 114. At this time, the catalyst passing time of the raw material gas was 2.38 s for each of the Examples and Comparative Examples.

The reaction product flowing out from the reactor was quantitatively analyzed by the same method as in Example 4, and the $CO_2$ conversion ratio, CO selectivity and hydrocarbon selectivity were calculated. The results are shown in Table 2.

106: Heater
107: Bypass pipe
108: Reactor
109: Branch outflow pipe
110: Cooling container
112: Valve
114: Back pressure regulator
116: Water trap
118: Valve
120: 6-way valve
126: 6-way valve
128: Film flow meter

The invention claimed is:

1. A hydrocarbon synthesis catalyst for reacting a raw material gas comprising hydrogen and carbon dioxide to convert to hydrocarbons, wherein when elemental analysis of a surface of the hydrocarbon synthesis catalyst to be brought into contact with the raw material gas is performed by energy dispersive X-ray spectroscopy (SEM-EDX), 15 to 65% by mass of Fe, 10 to 40% by mass of O, 0.04 to 30% by mass of Na, 1 to 15% by mass of Ni, and 5 to 30% by mass of Cr are detected.

2. The hydrocarbon synthesis catalyst according to claim 1, wherein when the surface of the hydrocarbon synthesis catalyst to be brought into contact with the raw material gas is analyzed by an X-ray diffraction method, oxides with Fe valences of +2 and/or +3 are detected.

3. The hydrocarbon synthesis catalyst according to claim 1, wherein when the surface of the hydrocarbon synthesis catalyst to be brought into contact with the raw material gas

TABLE 2

| | | Unit | Compartive Example 1 | Compartive Example 2 | Example 5 | Example 6 | Example 7 |
|---|---|---|---|---|---|---|---|
| Material Pretreatment | Catalyst raw material | — | SUS316L | SUS630 | SUS316L | SUS316L | SUS316L |
| | Pickling (same conditions as in Example 4) | — | None | None | Yes | Yes | Yes |
| | NaNO3 concentration in Na impregnation | mol/L | None | None | 0.1 | 0.3 | 0.5 |
| Catalyst performance | $CO_2$ conversion rate | % by volume | 23.8 | 19.0 | 23.0 | 27.0 | 30.4 |
| | CO selectivity | % by volume | 19.8 | 20.9 | 33.8 | 34.2 | 42.0 |
| | $CH_4$ selectivity | % by volume | 75.2 | 72.2 | 43.2 | 52.1 | 55.4 |
| | $O_{2-4}$ selectivity | % by volume | 0.2 | 0.4 | 9.8 | 6.5 | 9.7 |
| | $O_{2-4}$ selectivity | % by volume | 13.5 | 21.6 | 13.2 | 10.1 | 12.2 |
| | $C_5^+$ selectivity | % by volume | 11.1 | 5.8 | 33.8 | 31.3 | 22.7 |

From the results in Table 2, it can be seen that the $CO_2$ conversion ratio and $C_5^+$ selectivity increased by impregnating the catalyst raw material with Na. It is also found that there is an optimum sodium compound concentration range in the Na impregnation for increasing the $C_5^+$ selectivity.

DESCRIPTION OF REFERENCE NUMERALS

10: Hydrocarbon synthesis catalyst
11: One end surface
12: The other end surface
13: Flow path
14: Surface of flow path
15: Protrusion
100: Hydrocarbon Synthesis device
101a: Pipe for $H_2$ and $N_2$
101b: Pipe for raw material gas
102a: Mass flow controller
102b: Mass flow controller
103: Gas supply pipe
105: Gas outflow pipe is analyzed by an X-ray diffraction method, a ratio $(I_2/I_1)$ is in a range of 0.02 to 3.0, in which $I_1$ is a peak area in a range of $2\theta=44°$ to 45° representative of Fe—Cr alloy, and $I_2$ is a peak area in a range of $2\theta=35°$ to 36° representative of $Fe_2O_3$.

4. The hydrocarbon synthesis catalyst according to claim 1, wherein when the surface of the hydrocarbon synthesis catalyst to be brought into contact with the raw material gas is analyzed by an X-ray diffraction method, a ratio $(I_3/I_1)$ is in a range of 0.02 to 0.5, in which $I_1$ is a peak area in a range of $2\theta=44°$ to 45° representative of Fe—Cr alloy, and $I_3$ is a peak area in a range of $2\theta=30°$ to 31° representative of $FeCr_2O_4$.

5. The hydrocarbon synthesis catalyst according to claim 1, wherein when elemental analysis of the surface of the hydrocarbon synthesis catalyst to be brought into contact with the raw material gas is performed by energy dispersive X-ray spectroscopy (SEM-EDX), 0.05 to 4% by mass of Na is detected.

6. The hydrocarbon synthesis catalyst according to claim 1, wherein when elemental analysis of the surface of the hydrocarbon synthesis catalyst to be brought into contact with the raw material gas is performed by energy dispersive X-ray spectroscopy (SEM-EDX), 2 to 9% by mass of Ni is detected.

7. The hydrocarbon synthesis catalyst according to claim 1, wherein the hydrocarbon synthesis catalyst is in a powder form.

8. The hydrocarbon synthesis catalyst according to claim 7, wherein a BET specific surface area of the hydrocarbon synthesis catalyst is 10 to 20 $m^2/g$.

9. The hydrocarbon synthesis catalyst according to claim 1, wherein the hydrocarbon synthesis catalyst is provided in a form of a shaped article comprising one or more flow paths penetrating from one end surface to the other end surface, wherein a surface of the one or more flow paths constitutes the surface of the hydrocarbon synthesis catalyst to be brought into contact with the raw material gas.

10. The hydrocarbon synthesis catalyst according to claim 9, wherein a BET specific surface area of the surface of the one or more flow paths is 5 to 15 $m^2/g$.

11. A method for manufacturing the hydrocarbon synthesis catalyst according to claim 1, the method comprising:

a step A1 of preparing a Fe-Cr alloy powder comprising 50 to 90% by mass of Fe, 10 to 20% by mass of Cr, and 1 to 20% by mass of Ni;

a step A2 of impregnating the powder with Na to obtain a Na-impregnated powder; and a step A3 of firing the Na-impregnated powder in an oxygen-containing atmosphere at 380 to 880° C., wherein the hydrocarbon synthesis catalyst is in a powder form.

12. The method for manufacturing the hydrocarbon synthesis catalyst according to claim 11, wherein the Fe-Cr alloy powder comprises 3 to 5% by mass of Ni.

13. The method for manufacturing the hydrocarbon synthesis catalyst according to claim 11, wherein the Fe-Cr alloy powder is SUS630.

14. The method for manufacturing the hydrocarbon synthesis catalyst according to claim 11, further comprising a step A4 of pickling the powder between the step A1 and the step A2.

15. A method for manufacturing the hydrocarbon synthesis catalyst according to claim 1, the method comprising:

a step B1 of preparing Fe-Cr alloy powder comprising 50 to 90% by mass of Fe, 10 to 20% by mass of Cr, and 1 to 20% by mass of Ni;

a step B2 of shaping the powder using an additive manufacturing method into a shaped article comprising one or more flow paths penetrating from one end surface to the other end surface;

a step B3 of impregnating a surface of the one or more flow paths of the shaped article with Na to obtain a Na-impregnated shaped article; and a step B4 of firing the Na-impregnated shaped article in an oxygen-containing atmosphere at 380 to 880° C., wherein a surface of the one or more flow paths constitutes the surface of the hydrocarbon synthesis catalyst to be brought into contact with the raw material gas.

16. The method for manufacturing the hydrocarbon synthesis catalyst according to claim 15, wherein the Fe-Cr alloy powder comprises 3 to 5% by mass of Ni.

17. The method for manufacturing the hydrocarbon synthesis catalyst according to claim 15, wherein the Fe-Cr alloy powder is SUS630.

18. The method for manufacturing the hydrocarbon synthesis catalyst according to claim 15, further comprising a step B5 of pickling the surface of the one or more flow paths of the shaped article between the step B2 and the step B3.

19. A method for synthesizing hydrocarbons, comprising contacting a raw material gas comprising hydrogen and carbon dioxide with the surface of the hydrocarbon synthesis catalyst according to claim 1 to be brought into contact with the raw material gas, thereby reacting the raw material gas.

* * * * *